United States Patent [19]

Morita et al.

[11] Patent Number: 6,136,331
[45] Date of Patent: Oct. 24, 2000

[54] COSMETIC PREPARATIONS CONTAINING FLUORINATED OILS

[75] Inventors: Masamichi Morita; Eiji Seki; Motonobu Kubo, all of Osaka, Japan

[73] Assignee: Daikin Industries LTD, Osaka, Japan

[21] Appl. No.: 09/214,153

[22] PCT Filed: Jul. 7, 1997

[86] PCT No.: PCT/JP97/02343

§ 371 Date: Dec. 29, 1999

§ 102(e) Date: Dec. 29, 1999

[87] PCT Pub. No.: WO98/01104

PCT Pub. Date: Jan. 15, 1998

[30] Foreign Application Priority Data

Jul. 8, 1996 [JP] Japan ................................ 8-177837

[51] Int. Cl.[7] ........................ A61K 7/00; A61K 9/14; A61K 7/025
[52] U.S. Cl. ..................... 424/401; 424/64; 424/489; 514/550; 514/746; 514/759
[58] Field of Search .................... 424/401, 489, 424/64; 514/550, 746, 759

[56] References Cited

FOREIGN PATENT DOCUMENTS

| 0633016A | 1/1995 | European Pat. Off. . |
|---|---|---|
| 3-246211A | 11/1991 | Japan . |
| 3-246212A | 11/1991 | Japan . |
| 3256211 | 11/1991 | Japan . |
| 5331019 | 12/1993 | Japan . |
| 7138130 | 5/1995 | Japan . |
| 8299782 | 11/1996 | Japan . |

*Primary Examiner*—Thurman K. Page
*Assistant Examiner*—Alysia Berman

[57] ABSTRACT

A cosmetic containing fluorine-containing oil represented by the following formula do not inhibit the oil repellency of powder treated with a fluorine-containing compound, is excellent in affinity for the skin, and is inexpensive.

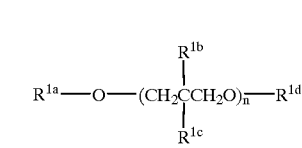

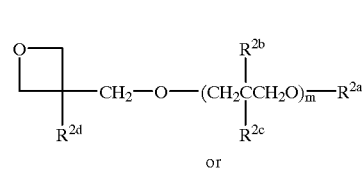

or

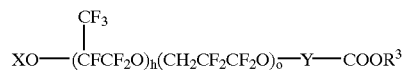

4 Claims, No Drawings

COSMETIC PREPARATIONS CONTAINING FLUORINATED OILS

This application is the national phase under 35 U.S.C. §371 of prior PCT International Application No. PCT/JP97/02343 which has an International filing date of Jul. 7, 1997 which designated the United States of America.

FIELD OF THE INVENTION

The present invention relates to a cosmetic comprising a fluorine-containing oil. The present invention relates to a cosmetic comprising a fluorine-containing oil which can be used in combination with a hydrocarbon-based oil and is incompatible with the hydrocarbon-based oil, and which can be used in combination with powder treated with a fluorine-containing compound and does not inhibit the oil repellency of the powder treated with fluorine-containing compound. In addition to these characteristics, the fluorine-containing oil is characterized by having high safety to skin and high affinity for skin and being inexpensive.

RELATED ART

In recent years, cosmetics into which perfluoropolyethers have been incorporated have been used in many cases. Perfluoropolyethers have the property (lipophobicity) that when used in combination with a hydrocarbon-based oil, they are incompatible with the hydrocarbon-based oil as well as the property that when used in combination with powder treated with a fluorine-containing compound, they do not inhibit the oil repellency of the powder treated with fluorine-containing compound. However, perfluoropolyethers were originally developed as a lubricant in a vacuum pump or the like and are not necessarily the most suitable for incorporation into cosmetics. Specifically, perfluoropolyethers are poor in affinity for skin due to complete replacement of hydrogen atoms in the polyethers by fluorine atoms, and are very expensive.

SUMMARY OF THE INVENTION

An object of the present invention is to provide a fluorine-containing oil which, when used in combination with powder treated with fluorine-containing compound, does not inhibit the oil repellency of the powder treated with fluorine-containing compound, is excellent in affinity for skin, and is inexpensive.

As result of extensive study for solving the above problems, the present inventors found that a specific fluorinated oil is equivalent to perfluoropolyethers in respect of (1) lipophobicity, (2) the property of not inhibiting the oil repellency of the powder treated with fluorine-containing compound and (3) safety for skin and is superior to perfluoropolyethers and in respect of (4) higher affinity for skin and (5) capability of production at lower costs due to incomplete fluorination.

The present invention provides a cosmetic comprising 0.01 to 100% by weight of a fluorine-containing oil (I) represented by the general formula:

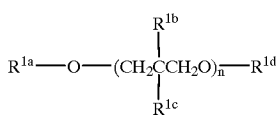

(I)

wherein $R^{1a}$ and $R^{1d}$ represent a hydrogen atom or a partially or completely fluorinated $C_1$–$C_{20}$ aliphatic group; $R^{1b}$ and $R^{1c}$ represent a hydrogen atom, a $C_1$–$C_{20}$ aliphatic group, or a partially or completely fluorinated $C_1$–$C_{20}$ aliphatic group, provided that at least one of $R^{1a}$ to $R^{1d}$ is a partially or completely fluorinated $C_1$–$C_{20}$ aliphatic group; and n is a number of 1 to 20.

Also, the present invention provides a cosmetic comprising 0.01 to 100% by weight of a fluorine-containing oil (II) represented by the general formula:

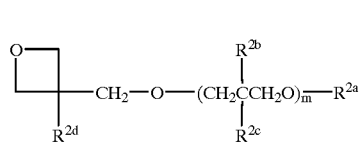

(II)

wherein $R^{2a}$ represents a hydrogen atom or a partially or completely fluorinated $C_1$–$C_{20}$ aliphatic group; $R^{2b}$, $R^{2c}$ and $R^{2d}$ represent a $C_1$–$C_{20}$ aliphatic group or a partially or completely fluorinated $C_1$–$C_{20}$ aliphatic group, provided that at least one of $R^{2a}$ to $R^{2d}$ is a partially or completely fluorinated $C_1$–$C_{20}$ aliphatic group; and m is a number of 1 to 20.

Further, the present invention provides a cosmetic comprising 0.01 to 100% by weight of a fluorine-containing oil (III) represented by the general formula:

(III)

wherein X represents a hydrogen atom, a fluorine atom, a chlorine atom, a bromine atom, or a partially or completely fluorinated $C_1$–$C_{30}$ aliphatic group; Y represents a partially or completely fluorinated $C_1$–$C_{30}$ aliphatic group; and $R^3$ represents a $C_1$–$C_{22}$ aliphatic group; and h+o=1 to 100.

Furthermore, the present invention provides a cosmetic comprising 1 to 30% by weight of at least one selected from the group consisting of fluorine-containing oils (I), (II) and (III) and 5 to 95% by weight of powder treated with a fluorine-containing compound.

DETAILED DESCRIPTION OF THE INVENTION

In the present invention, the fluorine-containing oil (I), the fluorine-containing oil (II) and/or the fluorine-containing oil (III) are used.

In the general formulae (I), (II) and (III), if $R^{1a}$, $R^{1b}$, $R^{1c}$, $R^{1d}$, $R^{2a}$, $R^{2b}$, $R^{2c}$, $R^{2d}$, X and Y are a partially or completely fluorinated aliphatic group, these may possess an oxygen atom or an unsaturated bond (the partially fluorinated aliphatic groups may be e.g. $R^{10}CH_2$ group ($R^{10}$ is a partially or completely fluorinated aliphatic group such as an alkyl group.).). Examples of the partially or completely fluorinated aliphatic group include:

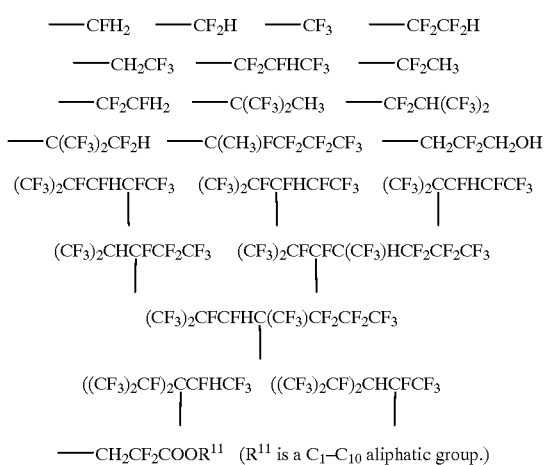

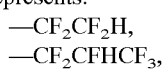 ($R^{11}$ is a $C_1$–$C_{10}$ aliphatic group.)

If $R^{1b}$, $R^{1c}$, $R^{2b}$, $R^{2c}$ and $R^{2d}$ are a $C_1$–$C_{20}$ aliphatic group, these may possess an oxygen atom. Examples of the $C_1$–$C_{20}$ aliphatic group are an alkyl group such as methyl, ethyl, n-propyl, isopropyl, n-butyl, isobutyl, sec-butyl and t-butyl and a hydroxyalkyl group such as hydroxymethyl and 2-hydroxyethyl (—CH$_2$CH$_2$OH).

$R^{1b}$, $R^{1c}$, $R^{2b}$ and $R^{2c}$ in the repeating units may be the same or different.

The number of carbon atoms in each of $R^{1a}$ to $R^{1d}$, $R^{2a}$ to $R^{1d}$, X and Y is preferably from 1 to 10, particularly 2 to 4.

Specific examples of the fluorine-containing oil (I) are as follows:

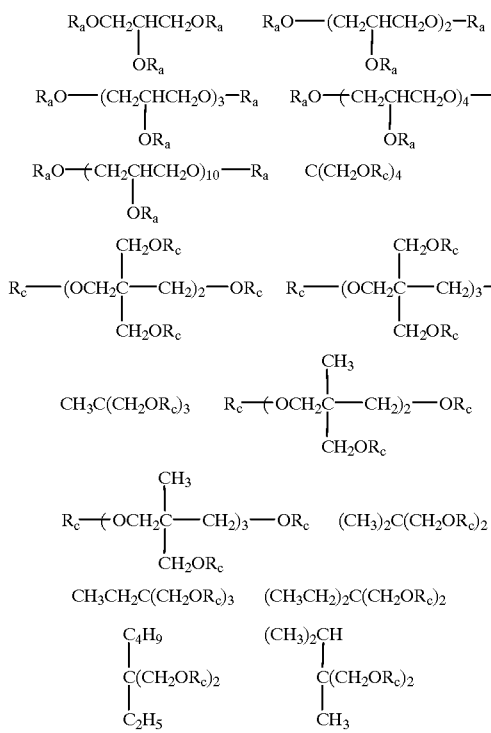

wherein each $R_a$ and $R_c$ is the same or different and represents:
- —CF$_2$CF$_2$H,
- —CF$_2$CFHCF$_3$,
- —CF$_2$CH$_3$,
- —CF$_2$CFH$_2$,
- —C(CF$_3$)$_2$CH$_3$,
- —CF$_2$CH(CF$_3$)$_2$,
- —C(CF$_3$)$_2$CF$_2$H,
- —C(CH$_3$)FCF$_2$CF$_3$.

Specific examples of the fluorine-containing oil are as follows:

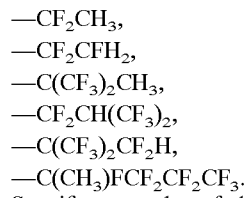
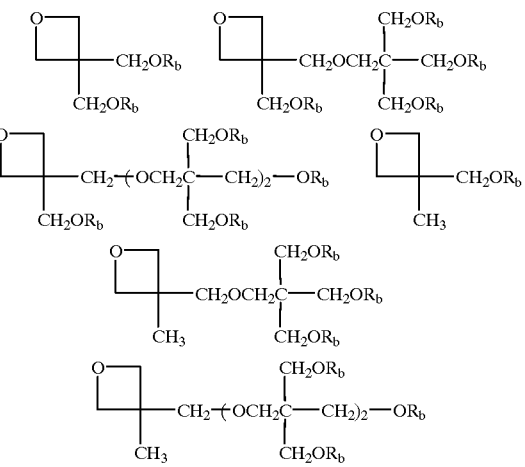
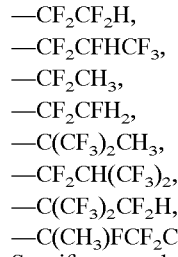

wherein each $R_b$ represents:
- —CF$_2$CF$_2$H,
- —CF$_2$CFHCF$_3$,
- —CF$_2$CH$_3$,
- —CF$_2$CFH$_2$,
- —C(CF$_3$)$_2$CH$_3$,
- —CF$_2$CH(CF$_3$)$_2$,
- —C(CF$_3$)$_2$CF$_2$H,
- —C(CH$_3$)FCF$_2$CF, Specific examples of the fluorine-containing oil (III) are as follows:

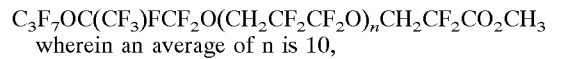
C$_3$F$_7$OC(CF$_3$)FCF$_2$O(CH$_2$CF$_2$CF$_2$O)$_n$CH$_2$CF$_2$CO$_2$CH$_3$
wherein an average of n is 10,

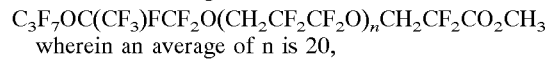
C$_3$F$_7$OC(CF$_3$)FCF$_2$O(CH$_2$CF$_2$CF$_2$O)$_n$CH$_2$CF$_2$CO$_2$CH$_3$
wherein an average of n is 20,

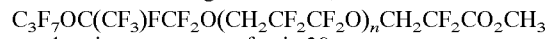
C$_3$F$_7$OC(CF$_3$)FCF$_2$O(CH$_2$CF$_2$CF$_2$O)$_n$CH$_2$CF$_2$CO$_2$CH$_3$
wherein an average of n is 30,

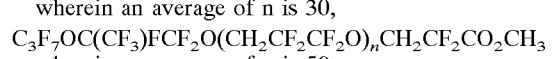
C$_3$F$_7$OC(CF$_3$)FCF$_2$O(CH$_2$CF$_2$CF$_2$O)$_n$CH$_2$CF$_2$CO$_2$CH$_3$
wherein an average of n is 50,

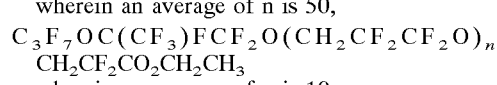
C$_3$F$_7$OC(CF$_3$)FCF$_2$O(CH$_2$CF$_2$CF$_2$O)$_n$CH$_2$CF$_2$CO$_2$CH$_2$CH$_3$
wherein an average of n is 10,

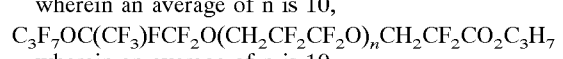
C$_3$F$_7$OC(CF$_3$)FCF$_2$O(CH$_2$CF$_2$CF$_2$O)$_n$CH$_2$CF$_2$CO$_2$C$_3$H$_7$
wherein an average of n is 10,

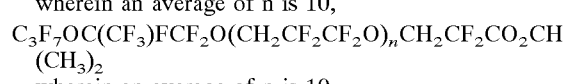
C$_3$F$_7$OC(CF$_3$)FCF$_2$O(CH$_2$CF$_2$CF$_2$O)$_n$CH$_2$CF$_2$CO$_2$CH(CH$_3$)$_2$
wherein an average of n is 10,

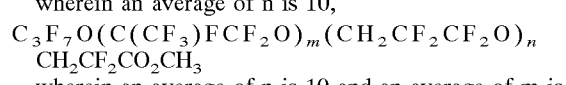
C$_3$F$_7$O(C(CF$_3$)FCF$_2$O)$_m$(CH$_2$CF$_2$CF$_2$O)$_n$CH$_2$CF$_2$CO$_2$CH$_3$
wherein an average of n is 10 and an average of m is 2, and

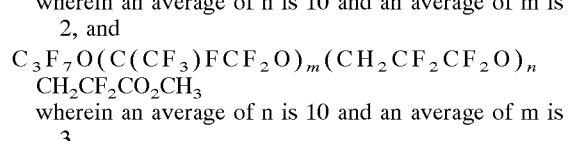
C$_3$F$_7$O(C(CF$_3$)FCF$_2$O)$_m$(CH$_2$CF$_2$CF$_2$O)$_n$CH$_2$CF$_2$CO$_2$CH$_3$
wherein an average of n is 10 and an average of m is 3.

The fluorine-containing oil (I) can be produced in various manners. For example, an alcohol compound and a fluorolefin are reacted as the starting materials whereby the fluorine-containing oil (I) can be synthesized. The alcohol compound as the starting material includes a wide variety of non-limiting compounds such as glycerin, diglycerin, polyglycerin, and compounds generally referred to as a hindered alcohol and a hindered alcohol oligomer. For the reaction of the alcohol and the fluorolefin as the starting materials, a solvent is preferably used. The solvent may be an aprotic polar solvent, and examples of the solvent are DMF (dimethylformamide), DMSO (dimethyl sulfoxide), NMP (N-methyl pyrrolidone), sulfolane, diglyme, triglyme, ether, THF, chloroform, dichloromethane, methyl ethyl ketone and acetone. Water may be added to the reaction solution. A reaction catalyst may be used. If HF is generated as a by-product, a basic catalyst may be used as a capturing agent therefor. Examples of the basic catalyst are an inorganic base such as KOH, NaOH, $K_2CO_3$, $Na_2CO_3$ and $NaHCO_3$ and an organic base such as triethylamine and tributylamine.

The reaction temperature may be from −10 to 200° C., preferably from 0 to 150° C. and most preferably from 10 to 120° C. The reaction pressure is not particularly limited, but is preferably from 0 to 20 kg/cm²G (gauge pressure), more preferably from 0 to 10 kg/cm²G. The reaction time may be from 0.5 to 100 hours, preferably from 2 to 50 hours.

The fluorine-containing oil (II) can be synthesized in various manners. For example, an alcohol compound and a fluorolefin are reacted as the starting materials whereby the fluorine-containing oil (II) can be synthesized. The alcohol compound as the starting material includes a wide variety of non-limiting compounds, particularly compounds generally referred to as a hindered alcohol and a hindered alcohol oligomer. For the reaction of the alcohol and the fluorolefin as the starting materials, a solvent is preferably used. The solvent may be an aprotic polar solvent, and examples of the solvent are DMF, DMSO, NMP, sulfolane, diglyme, triglyme, ether, THF, chloroform and dichloromethane. Water may be added to the reaction solution. A reaction catalyst may be used. If HF is generated as a by-product, a basic catalyst may be used as a capturing agent therefor. Examples of the basic catalyst are an inorganic base such as KOH, NaOH, $K_2CO_3$, $Na_2CO_3$ and $NaHCO_3$ and an organic base such as triethylamine and tributylamine.

The reaction temperature may be from −10 to 200° C., preferably from 0 to 150° C. and most preferably from 10 to 120° C. The reaction pressure is not particularly limited, but is preferably from 0 to 20 kg/cm²G, more preferably from 0 to 10 kg/cm²G. The reaction time may be from 0.5 to 100 hours, preferably from 2 to 50 hours.

The fluorine-containing oil (III) can be synthesized in various manners. For example, pentafluoropropionyl fluoride or hexafluoropropylene oxide oligomer acid fluoride and tetrafluoroxetane are reacted in the presence of a catalyst, followed by reaction with an alcohol compound, or reduction, or fluorination whereby the fluorine-containing oil (III) can be synthesized. Alternatively, tetrafluoroxetane is subjected to a ring-opening polymerization by use of an initiator such alkali metal halide or both an alkali metal fluoride and acyl fluoride, and hexafluoropropylene oxide is introduced into the system, followed by reaction of the resulting compound with an alcohol compound, or reduction, or fluorination whereby the fluorine-containing oil (III) can be synthesized. A solvent may be an aprotic polar solvent. Examples of the solvent are DMF, DMSO, NMP, sulfolane, acetonitrile, diglyme, triglyme, tetraglyme and crown ether. The reaction catalyst is preferably KF, CsF, KI, KBr or the like. The alcohol compound used includes non-limiting lower alcohols such as methyl alcohol and ethyl alcohol.

Not only one of these fluorine-containing oils but a combination thereof can also be incorporated into the cosmetic, or these may be mixed with perfluoropolyethers. The fluorine-containing oil of the present invention can be used in a finishing cosmetic such as foundation cream, face powder, cheek color and eye color, a basal cosmetic such as face lotion, milky lotion and cream, a hair care product such as rinse and treatment liquid, a lipstick overcoat, a UV care cosmetic and the like. The fluorine-containing oil can be used in an amount of 0.01 to 100% by weight based on the cosmetic. The cosmetic comprising the fluorine-containing oil can be produced in a conventional method.

The cosmetic of the present invention is particularly effective when it contains:

(a) 1 to 30% by weight of at least one selected from the group consisting of the fluorine-containing oils (I), (II) and (III), and (b) 5 to 95% by weight of powder treated with a fluorine-containing compound.

The balance of the cosmetic is other components necessary for making the cosmetic. The cosmetic may contain other components such as a fluorine-free oil and powder other than powder treated with the fluorine-containing compound, as well as a silicone, a hydrocarbon-based oil, a preservative and/or a perfume.

The content of the fluorine-containing oil is preferably from 2 to 20% by weight, more preferably from 5 to 15% by weight.

The content of the powder treated with fluorine-containing compound is preferably from 5 to 20% or from 70 to 95% by weight.

The powder treated with fluorine-containing compound used in the present invention can be obtained by treating powder with a fluorine-containing compound such as polyfluoroalkyl phosphoric acids (or salts thereof), fluoroalkyldi(oxyethyl)amine phosphate esters, fluoroalkyl phosphate esters, and perfluoroalkyl group-containing polymers.

The polyfluoroalkyl phosphoric acids (or salts thereof) may be those described in U.S. Pat. No. 3,632,744 and may be e.g. compounds represented by the formula:

$$[C_mF_{2m+1}C_nH_{2n}O]_yPO(OM)_{3-y}$$

wherein M is a hydrogen atom, an alkali metal, ammonium or substituted ammonium; m and n each is an integer of 1 to 20; and the average of y is from 1.0 to 2.5.

The fluoroalkyldi(oxyethyl)amine phosphate esters may be those described in Japanese Laid-Open Patent Publication No. 250,074/1987 and may be compounds represented by e.g. the formula:

$$[C_nF_{2n+1}CH_2CH_2O]_qPO[ON(H_2)(CH_2CH_2OH)_2]_{3-q}$$

wherein n is an integer of 1 to 20, and q is 1 or 2.

The fluoroalkyl phosphate esters may be those described in Japanese Laid-Open Patent Publication No. 124,932/1993 and may be compounds represented by e.g. the formula:

$$(C_nF_{2n+1}CH_2CH_2O)_mPO(OH)_{3-m}$$

wherein m is an integer of 1 to 3, and n is an integer of 4 to 20.

The perfluoroalkyl group-containing polymers may be those described in Japanese Laid-Open Patent Publication No. 167,209/1980 and may be a homopolymer of a perfluoroalkyl group-containing (meth)acrylate, or a copolymer between a perfluoroalkyl group-containing (meth)acrylate and a monomer having a double bond (such as acrylate ester, maleic anhydride, chloroprene, butadiene and methyl vinyl ketone).

The powder to be treated includes inorganic powder such talc, kaolin, mica, titanium mica, titanium oxide, iron oxide, magnesium oxide, zinc monoxide, zinc dioxide, heavy or light calcium carbonate, dibasic calcium phosphate, aluminum hydroxide, barium sulfate, silica, alumina, silica gel, carbon black, antimony oxide, magnesium silicate aluminate, magnesium metasilicate aluminate and synthetic mica; and organic powder such as protein powder, fish scale guanine, metal soap, polyvinyl chloride, nylon 12, microcrystalline fiber powder, tar pigment and lake.

In the cosmetic described below, an oil may consist of the fluorine-containing oil or may be a mixture of the fluorine-containing oil and fluorine-free oil.

Examples of the fluorine-free oil are solid or semisolid oils including vaseline, lanolin, ceresin, microcrystalline wax, carnauba wax, candelilla wax, higher fatty acids and higher alcohols; and fluid oils such as squalane, liquid paraffin, ester oil, diglyceride, triglyceride and silicone oil.

If the cosmetic is powder foundation, face powder, cheek color or eye color, the powder foundation, face powder, cheek color and eye color may comprise:

1 to 30% by weight of an oil,
5 to 95% by weight of powder treated with fluorine-containing compound,
5 to 95% by weight of silicone-treated powder and/or untreated powder,
1% by weight or less of a preservative, and
1% by weight or less of a perfume.

If the cosmetic is liquid foundation, the liquid foundation may comprise:

1 to 10% by weight of an oil,
5 to 30% by weight of powder treated with fluorine-containing compound,
5 to 30% by weight of silicone-treated powder and/or untreated powder,
1% by weight or less of a water-soluble polymer, 80% by weight or less of water,
1% by weight or less of a preservative, and
1% by weight or less of a perfume.

If the cosmetic is face lotion, the face lotion may comprise:

0.01 to 10% by weight of an oil,
10% by weight or less of an organic solvent (e.g. alcohol),
5% by weight or less of an emulsifier,
1% by weight or less of a preservative,
1% by weight or less of a perfume, and
99% by weight or less of water. The alcohol may be a monohydric alcohol, a dihydric alcohol and a trihydric alcohol.

If the cosmetic is lotion, the lotion may comprise:
0.01 to 20% by weight of an oil,
5% by weight or less of an emulsifier,
1% by weight or less of a preservative,
1% by weight or less of a perfume, and
95% by weight or less of water.

If the cosmetic is cream, the cream may comprise:
0.01 to 95% by weight oil,
10% by weight or less of an emulsifier,
1% by weight or less of a preservative,
1% by weight or less of a perfume, and
80% by weight or less of water.

If the cosmetic is rinse, the rinse may comprise:
0.01 to 10% by weight of an oil,
10% by weight or less of a cationic surface active agent,
5% by weight or less of a emulsifier,
1% by weight or less of a preservative,
1% by weight or less of a perfume, and
95% by weight or less of water.

If the cosmetic is lip-stick overcoat, it may comprise:
80 to 100% by weight of an oil,
20% by weight or less of silica powder and/or alumina powder.

PREFERRED EMBODIMENTS OF THE INVENTION

The present invention will be illustrated with reference to the following Examples which do not limit the invention.

PREPARATIVE EXAMPLE 1

Production of Oil (a) (corresponding to fluorine-containing oil (I))

Diglycerin (55.4 g), dimethyl sulfoxide (300 mL) and KOH (10 g) were introduced into a 500 mL SUS autoclave, and under stirring at room temperature, tetrafluoroethylene (TFE) was introduced into the liquid phase until the pressure reached 4 kg/cm$^2$G. After stirring for 10 hours (reaction temperature: 80° C.), the unreacted TFE was purged away, then 100 mL of chloroform was added, and the product was washed with 5% HCl aqueous solution and 10% NaHCO$_3$ aqueous solution, dried over magnesium sulfate anhydride and filtered, followed by distilling away the solvent from the filtrate under reduced pressure to give 138.0 g of the following colorless oily substance (a) corresponding to fluorine-containing oil (I):

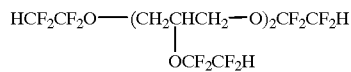

PREPARATIVE EXAMPLE 2

Production of Oil (b) (corresponding to fluorine-containing oil (I))

Pentaerythritol (30 g), NaOH (0.9 g) and dimethyl sulfoxide (200 mL) were introduced into a 500 mL SUS autoclave, then the atmosphere was replaced by nitrogen and the pressure was reduced followed by introducing hexafluoropropane (132 g) into the autoclave. While hexafluoropropane was further added as it was consumed, the mixture was reacted as a reaction temperature increases (reaction temperature: 80° C.). After the completion of the reaction (reaction time: 12 hours), the product was extracted with HCFC-141b and washed with water, then with 1 N HCl aqueous solution and with a saturated saline solution. An organic layer was dried over magnesium sulfate anhydride and filtered, followed by distilling away the solvent from the filtrate under reduced pressure to give 150 g of the following colorless oily substance (b) corresponding to fluorine-containing oil (I):

PREPARATIVE EXAMPLE 3

Production of Oil (c) (corresponding to fluorine-containing oil (I))

Trimethylolethane (30 g), KOH (49.3 g) and dimethyl sulfoxide (150 mL) were introduced into a 500 mL SUS autoclave, then the atmosphere was replaced by nitrogen and the pressure was reduced followed by introducing tetrafluoroethylene (TFE) (75 g) into the autoclave. While TFE was further added as it was consumed, the mixture was reacted as a reaction temperature increases (reaction temperature: 80° C.). After the completion of the reaction (reaction time: 8 hours), the product was extracted with HCFC-141b and washed with water, with 1 N HCl aqueous solution and with a saturated saline solution. The organic layer was dried over magnesium sulfate anhydride and filtered, followed by distilling away the solvent from the filtrate under reduced pressure to give 100 g of the following colorless oily substance (c) corresponding to fluorine-containing oil (I):

$CH_3C(CH_2OCF_2CF_2H)_3$

PREPARATIVE EXAMPLE 4

Production of Oil (d) (corresponding to fluorine-containing oil (I)) and Oil (e) (fluorine-containing oil (II))

Dipentaerythritol (150 g), KOH (39 g) and dimethyl sulfoxide (450 mL) were introduced into a 1 L autoclave, then the atmosphere was replaced by nitrogen and the pressure was reduced followed by introducing tetrafluoroethylene (TFE) (437 g) into the autoclave. While TFE was further added as it was consumed, the mixture was reacted at 80° C. for 12 hours. After the completion of the reaction, the product was extracted with HCFC-141b and washed with water, then with 1 N HCl aqueous solution and with a saturated saline solution. The organic layer was dried over sodium sulfate anhydride, filtered, and concentrated at 50° C. under reduced pressure to give a colorless oily substance (435 g).

The resulting oil was composed of the following compound (d) corresponding to fluorine-containing oil (I):

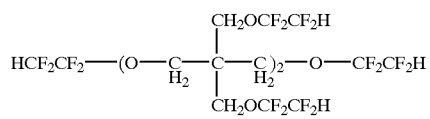

and the following compound (e) corresponding to fluorine-containing oil (II):

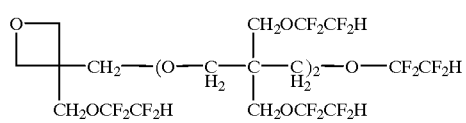

wherein the weight ratio of compound (d)/compound (e) was 67/33.

PREPARATIVE EXAMPLE 5

Production of Oil (f) (corresponding to fluorine-containing oil (III))

Diglyme (500 mL) previously dehydrated and dry CsF (15.2 g) were introduced into a 1 L flask and stirred. Then, $C_3F_7OC(CF_3)FCOF$ (6FO dimer) (33.2 g) was added thereto and stirred to give a homogeneous mixture, and tetrafluoroxetane (130 g) was added dropwise thereto for reaction. After dropwise addition over the period of 20 hours, the mixture was stirred for two hours (reaction temperature: 20° C.), and the reaction solution was analyzed by gas chromatography, to indicate disappearance of a tetrafluoroxetane peak. After methanol (50 g) was added to the resulting reaction mixture, diglyme was removed by evaporation under reduced pressure whereby the following colorless oily compound (f) (151 g) corresponding to fluorine-containing oil (III) was obtained.

Compound (f): $C_3F_7OC(CF_3)FCF_2O(CH_2CF_2CF_2O)_n CH_2CF_2CO_2CH_3$ [average of n=10]

COMPARATIVE PREPARATIVE EXAMPLE 1

Lipophobicity-Free Fluorine-Containing Oil (6FO) 3PPG 67.8 g of polypropylene glycol (molecular weight: 2,000), 4.7 g of pyridine, 53 g of dichloromethane were introduced into a 300 mL round flask, and the following compound:

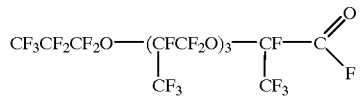

[hereinafter referred to as (6FO)3] was added dropwise to the flask through a dropping funnel. After stirred at room temperature for 2 hours, the product was washed with 0.1 N aqueous hydrochloric acid solution and purified water, and dried over magnesium sulfate to give (6FO)3PPG having the following structural formula:

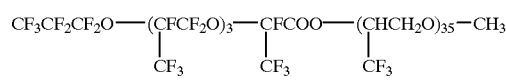

PREPARATIVE EXAMPLE 6 (powder treated with fluorine-containing compound)

A dispersion of 133.3 g of commercially available perfluoroalkyl phosphate ester diethanolamine salt (Unidine TG-101 (solid content of 15%) manufactured by Daikin Industries Ltd.) in 2000 g of water was mixed with 400 g of mixture powder (containing titanium oxide, iron oxide yellow, iron oxide red, iron oxide black, talc and sericite mixed in the weight ratio of 15.3/3.3/1.0/1.0/38.0/41.6) for 3 minutes in a juicer mixer. The mixture was adjusted to pH 3 or less with the addition of dilute hydrochloric acid and filtered under suction. The product was dried under heating at 60° C. for 24 hours, ground with a speed cutter for 30 seconds to give powder treated with fluorine-containing compound.

EXAMPLES 1 TO 5 AND COMPARATIVE EXAMPLES 1 (evaluation of lipophobicity)

The fluorine-containing oils obtained in Preparative Examples 1 to 5 (Examples 1 to 5) and Comparative Preparative Example 1 (Comparative Example 1) were evaluated for lipophobicity. Lipophobicity was evaluated as follows: 50 mg of fluorine-containing oil was added to 5 g of liquid paraffin, shaken, and left for 10 minutes, and the state of the fluorine-containing oil was observed to evaluate the lipophobicity of the fluorine-containing oil.

○: Lipophobic (complete precipitation of the fluorine-containing oil)

Δ: Slightly lipophobic (dispersion of the fluorine-containing oil)

X: Not lipophobic (dissolution of the fluorine-containing oil)

The evaluation results are shown in Table 1.

TABLE 1

| Example | Preparative Example | Type | Lipophobicity |
|---|---|---|---|
| Example 1 | Preparative Example 1 | Oil (a) | ○ |
| Example 2 | Preparative Example 2 | Oil (b) | ○ |
| Example 3 | Preparative Example 3 | Oil (c) | ○ |
| Example 4 | Preparative Example 4 | Oil (d) + oil (e) | ○ |
| Example 5 | Preparative Example 5 | Oil (f) | ○ |
| Com. Ex. 1 | Com. Prep. Example 1 | Lipophobicity-free fluorine-containing oil ((6FO)3PPG) | X |

EXAMPLES 6 TO 10 AND COMPARATIVE EXAMPLE 2 (evaluation of the property of not inhibiting the oil repellency of the powder treated with fluorine-containing compound)

100 g of each of the fluorine-containing oils in Preparative Examples 1 to 5 (Examples 6 to 10) and in Comparative Preparative Example 1 (Comparative Example 2) was mixed with 900 g of the powder treated with fluorine-containing compound prepared in Preparative Example 6 in a Henschel mixer, and the resulting powder was evaluated in an oil repellency test.

Oil repellency test: The powder was applied uniformly onto a filter paper, and 8 types of oil having different levels of surface tension, as shown in Table 2, were dropped on the paper. Oil repellency was assigned to a point of less than X (i.e. the point of oil which was not completely absorbed into the paper at 1 minute after the oil was dropped).

Evaluation Criteria:

○: Complete repulsion

X: Complete absorption at 1 minute after dropped.

TABLE 2

Oils used in the oil repellency test

| Point | Type | γ (mN/m) (25° C.) |
|---|---|---|
| 1 | Liquid paraffin | 31.2 |
| 2 | HD/liquid paraffin | 29.6 |
| 3 | Hexadecane (HD) | 27.3 |
| 4 | Tetradecane | 26.7 |
| 5 | Dodetane | 25.0 |
| 6 | Decane | 23.5 |
| 7 | Octane | 21.8 |
| 8 | Heptane | 20.0 |

The evaluation results are shown in Table 3.

TABLE 3

Property of not inhibiting the oil repellency of powder treated with fluorine-containing compound

| Example | Preparative Example | Name | Lipophobicity |
|---|---|---|---|
| Example 6 | Preparative Example 1 | Oil (a) | 5 |
| Example 7 | Preparative Example 2 | Oil (b) | 5 |
| Example 8 | Preparative Example 3 | Oil (c) | 5 |
| Example 9 | Preparative Example 4 | Oil (d) + oil (e) | 5 |
| Example 10 | Preparative Example 5 | Oil (f) | 5 |
| Comparative Example 2 | Com. Prep. Example 1 | Lipophobicity-free fluorine-containing oil ((6FO)3PPG) | 1 |
|  |  | Powder treated with fluorine-containing compound only | 5 |

EXAMPLES 11 TO 15 AND COMPARATIVE EXAMPLES 3 TO 5 (evaluation of affinity for skin)

The fluorine-containing oils in Preparative Examples 1 to 5 (Examples 11 to 15) and in Comparative Preparative Example 1 (Comparative Example 3) and commercially available perfluoropolyether Fomblin HC-04 (manufactured by Montefluoth) (Comparative Example 4), and Demnum S-20 (manufactured by Daikin Industries Ltd.) (Comparative Example 5) were evaluated for affinity for skin. Each fluorine-containing oil was applied directly onto the skin and evaluated for affinity for the skin according to the following criteria, as compared with the perfluoropolyether of Comparative Example 4.

Very good for the skin: ○○

Good: ○

Similar: Δ

Slightly inferior: X

Significantly inferior: XX

Evaluation was conducted by 5 specialists for organoleptic evaluation, and the results were expressed in terms of average. The evaluation results are shown in Table 4.

TABLE 4

Affinity for skin

| Example | Preparative Example | Name | Affinity |
|---|---|---|---|
| Example 11 | Preparative Example 1 | oil (a) | ○○ |
| Example 12 | Preparative Example 2 | oil (b) | ○○ |
| Example 13 | Preparative Example 3 | oil (c) | ○○ |
| Example 14 | Preparative Example 4 | oil (d) + oil (e) | ○○ |
| Example 15 | Preparative Example 5 | oil (f) | ○○ |
| Comparative Example 3 | Com. Prep. Example 1 | Lipophobicity-free fluorine-containing oil ((6FO) 3PPG) | ○○ |
| Comparative Example 4 |  | Fomblin HC-04 | Δ |
| Comparative Example 5 |  | Demnum S-20 | Δ |

EXAMPLES 16 TO 20 AND COMPARATIVE EXAMPLES 6 AND 7 (powdery foundation)

TABLE 5

| Starting material | | Powdery foundation | % by weight |
|---|---|---|---|
| (1) | Titanium oxide treated with fluorine-containing compound | | 10 |
| (2) | Iron oxide yellow treated with fluorine-containing compound | | 2.3 |
| (3) | Iron oxide red treated with fluorine-containing compound | | 0.65 |
| (4) | Iron oxide black treated with fluorine-containing compound | | 0.35 |
| (5) | Sericite treated with fluorine-containing compound | | 20 |
| (6) | Talc treated with fluorine-containing compound | | 56.6 |
| (7) | Preservative | | 0.1 |
| (8) | Fluorine-containing oil | | 10 |

In Table 5, the powder treated with fluorine-containing compounds as components (1) to (6) were those treated with 5% by weight of perfluoroalkyl ethyl phosphate ester diethanolamine salt:

(average of m=3.5, average of n=1.7)

Components (1) to (7) were mixed and ground with an atomizer and transferred to a Henschel mixer, and component (8) was added thereto and mixed uniformly. The mixture was introduced into a mold and press-molded to give a powdery foundation.

In the powdery foundation having the composition shown in Table 5, the fluorine-containing oil in each of Preparative Examples 1 to 5 was used as the component (8) and their corresponding compositions were regarded as Examples 16 to 20 respectively. Each of dimethylpolysiloxane (100 sc) and perfluoropolyether (Demnum S-20) was used in place of component (8) and their corresponding compositions were regarded as Comparative Examples 6 and 7 respectively. Examples 16 to 20 and Comparative Example 7 (Demnum S-20) could be press-molded, but Comparative Example 6 (dimethylpolysiloxane (100 sc)) could not molded. Examples 16 to 20 were superior to Comparative Example 7 (Demnum S-20) in respect of the adhesion of the foundation to the skin.

EXAMPLES 21 TO 25 AND COMPARATIVE EXAMPLE 8 (eye color)

TABLE 6

| Starting material | | Eye color | % by weight |
|---|---|---|---|
| (1) | Titanium mica treated with fluorine-containing compound | | 5 |
| (2) | Sericite treated with fluorine-containing compound | | 29.8 |
| (3) | Mica treated with fluorine-containing compound | | 25 |

TABLE 6-continued

| Starting material | | Eye color | % by weight |
|---|---|---|---|
| (4) | Colored pigment treated with fluorine-containing compound | | 25 |
| (5) | Fluorine-containing oil | | 15 |
| (6) | Preservative | | 0.1 |
| (7) | Perfume | | 0.1 |

The powder treated with fluorine-containing compound as components (1) to (4) were those treated with 5% by weight of perfluoroalkyl ethyl phosphate ester diethanolamine salt:

(average of m=3.5, average of n=1.7)

Components (1) to (4) were mixed and ground with an atomizer and transferred to a Henschel mixer, and components (5) to (7) were added thereto and mixed uniformly. The mixture was introduced into a mold and press-molded to give an eye color.

In the eye color composition shown in Table 6, each of the fluorine-containing oils in Preparative Examples 1 to 5 was used as component (5) and their corresponding compositions were regarded as Examples 21 to 25 respectively. Perfluoropolyether (Demnum S-20) was used in place of component (5) and its corresponding composition was regarded as Comparative Example 8. Examples 21 to 25 were superior to Comparative Example 8 in respect of the adhesion of the eye color to the skin.

EXAMPLES 26 TO 30 AND COMPARATIVE EXAMPLE 9 (liquid foundation)

TABLE 7

| Starting material | | Liquid foundation | % by weight |
|---|---|---|---|
| (1) | Titanium oxide treated with fluorine-containing compound | | 2.2 |
| (2) | Iron oxides (red, black, yellow) treated with fluorine-containing | | 0.7 |
| (3) | Sericite treated with fluorine-containing compound | | 5 |
| (4) | Talc treated with fluorine-containing compound | | 12.1 |
| (5) | Preservative | | 0.1 |
| (6) | Squalane | | 2 |
| (7) | Fluorine-containing oil | | 10 |
| (8) | Sorbitan monooleate | | 1 |
| (9) | Sucrose fatty ester (HLB16) | | 2 |
| (10) | Carboxyl vinyl polymer (1% aqueous solution) | | 40 |
| (11) | Glycerin | | 7 |
| (12) | Perfume | | 0.1 |
| (13) | Purified water | | 17.8 |

The powder treated with fluorine-containing compound as components (1) to (4) were those treated with 5% by weight of perfluoroalkyl ethyl phosphate ester diethanolamine salt:

(average of m=3.5, average of n=1.7)

Components (1) to (4) were mixed and ground, and components (5) to (13) were added and uniformly emulsified to give an objective liquid foundation.

In the liquid foundation composition shown in Table 7, the fluorine-containing oil in each of Preparative Examples 1 to 5 was used as component (7) and their corresponding compositions were regarded as Examples 26 to 30 respectively. Perfluoropolyether (Demnum S-20) was used in place of component (7) and its corresponding composition was regarded as Comparative Example 9. Examples 26 to 30 were superior to Comparative Example 9 in respect of the adhesion of the foundation to the skin.

EXAMPLES 31 TO 35 AND COMPARATIVE EXAMPLE 10 (lipstick overcoat)

TABLE 8

Lipstick overcoat

| Starting material | | % by weight |
|---|---|---|
| (1) | Fluorine-containing oil | 98 |
| (2) | Silica | 2 |

Components (1) and (2) were mixed uniformly to give a lipstick overcoat.

In the lipstick overcoat composition shown in Table 8, the fluorine-containing oil in each of Preparative Examples 1 to 5 was used as component (1) and their corresponding compositions were regarded as Examples 31 to 35 respectively. Perfluoropolyether (Demnum S-20 (manufactured by Daikin Industries Ltd.)) was used in place of component (1) and its corresponding composition was regarded as Comparative Example 10. Examples 31 to 35 were superior to Comparative Example 10 in respect of the adhesion of the lipstick overcoat to the skin.

EXAMPLES 36 TO 40 AND COMPARATIVE EXAMPLE 11 (skin cream)

TABLE 9

Skin cream

| Starting material | | % by weight |
|---|---|---|
| (1) | Sodium N-stearoyl-L-glutamate | 0.4 |
| (2) | Cetyl alcohol | 3 |
| (3) | Vaseline | 3 |
| (4) | Stearate monoglyceride | 3 |
| (5) | Lanolin | 3 |
| (6) | Fluorine-containing oil | 10 |
| (7) | Sorbitan sesquioleate | 0.5 |
| (8) | Polyoxyethylene polyoxy propylene block copolymer (Pluronic F-68) | 3 |
| (9) | Perfume | 0.1 |
| (10) | 1,3-butylene glycol | 8 |
| (11) | Preservative | 0.1 |
| (12) | Glycerin | 10 |
| (13) | Purified water | balance |

Components (1) to (9) were heated and mixed, and heated and dissolved components (10) to (13) were added thereto, and the mixture was emulsified uniformly and cooled to give an objective cream.

In the cream composition shown in Table 9, the fluorine-containing oil in each of Preparative Examples 1 to 5 was used as component (6) and their corresponding compositions were regarded as Examples 36 to 40 respectively. Perfluoropolyether (Demnum S-20 (manufactured by Daikin Industries Ltd.)) was used in place of component (6) and its corresponding composition was regarded as Comparative Example 11. Examples 36 to 40 were superior to Comparative Example 11 in respect of the penetration of the cream into the skin.

EXAMPLES 41 TO 45 AND COMPARATIVE EXAMPLE 12 (face lotion)

TABLE 10

Face lotion

| Starting material | | % by weight |
|---|---|---|
| (1) | Polyoxyethylene (20) sorbitan monolaurate | 0.4 |
| (2) | Perfume | 3 |
| (3) | Ethanol | 3 |
| (4) | 1,3-butylene glycol | 3 |
| (5) | Glycerin | 3 |
| (6) | Preservative | 10 |
| (7) | Fluorine-containing oil | 0.5 |
| (8) | Purified water | balance |

Components (1) to (3) and (7) were mixed and dissolved, and components (4), (5), (6) and (8) were mixed, dissolved, and added thereto, and the mixture was emulsified uniformly to give an objective face lotion.

In the face lotion composition shown in Table 10, the fluorine-containing oil in each of Preparative Examples 1 to 5 was used as component (7) and regarded as Examples 41 to 45 respectively. Perfluoropolyether (Demnum S-20 (manufactured by Daikin Industries Ltd.)) was used as component (7) and regarded as Comparative Example 12. Examples 41 to 45 were superior to Comparative Example 12 in respect of the penetration of the face lotion into the skin.

EXAMPLES 46 TO 50 AND COMPARATIVE EXAMPLE 13 (hair rinse)

TABLE 11

Hair rinse

| Starting material | | % by weight |
|---|---|---|
| (1) | Stearyl trimethyl ammonium chloride | 3 |
| (2) | Cetyl alcohol | 2 |
| (3) | Fluorine-containing oil | 2 |
| (4) | Preservative | 0.1 |
| (5) | Glycerin | 5 |
| (6) | Perfume | Suitable amount |
| (7) | Pigment | Suitable amount |
| (8) | Polyoxyethylene (10) sorbitan monooleate | 2 |
| (9) | Purified water | balance |

Components (1) to (9) were mixed, dissolved at 80° C., and left to be cooled to room temperature to give a hair rinse.

In the above hair rinse, the fluorine-containing oil in each of Preparative Examples 1 to 5 was used as component (3)

and their corresponding compositions were regarded as Examples 46 to 50 respectively. Perfluoropolyether (Demnum S-20 (manufactured by Daikin Industries Ltd.)) was used in place of component (3) and its corresponding composition was regarded as Comparative Example 13. Examples 46 to 50 were superior to Comparative Example 13 in respect of the penetration of the hair rinse into hair.

EXAMPLES 51 TO 55 AND COMPARATIVE EXAMPLE 14 (sunscreen milky lotion)

TABLE 12

Sunscreen milky lotion

| Starting material | | % by weight |
|---|---|---|
| (1) | Octamethyl cyclotetrasiloxane | 35 |
| (2) | Fluorine-containing oil | 5 |
| (3) | Dimethylpolysiloxane-polyoxyalkylene copolymer | 3 |
| (4) | Glycerin | 2 |
| (5) | Ethanol | 5 |
| (6) | Zinc oxide treated with fluorine-containing compound | 5 |
| (7) | Methoxy octyl cinnamate | 2 |
| (8) | Perfume | Trace amount |
| (9) | Water | balance |

The powder treated with fluorine-containing compound as component (6) was one treated with 7% by weight of perfluoroalkyl ethyl phosphate ester diethanolamine salt:

(average of m=3.5, average of n=1.7)

Components (1) to (3) were mixed and dissolved at room temperature, and component (6) was added thereto and dispersed by a disper. The mixture was emulsified under stirring to give an objective sunscreen milky lotion.

In the above sunscreen milky lotion, the fluorine-containing oil in each of Preparative Examples 1 to 5 was used as component (2) and their corresponding compositions were regarded as Examples 51 to 55 respectively. Perfluoropolyether (Demnum S-20 (manufactured by Daikin Industries Ltd.)) was used as component (2) and its corresponding composition was regarded as Comparative Example 14. Examples 51 to 55 were superior to Comparative Example 14 in respect of the adhesion to the skin and water resistance.

What is claimed is:

1. A cosmetic comprising 0.01 to 100% by weight of a fluorine-containing oil (I) represented by the general formula:

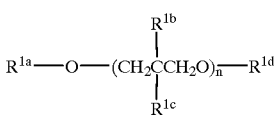

wherein $R^{1a}$ and $R^{1d}$ represent a hydrogen atom or a partially or completely fluorinated $C_1$–$C_{20}$ aliphatic group; $R^{1b}$ and $R^{1c}$ represent a hydrogen atom, a $C_1$–$C_{20}$ aliphatic group, or a partially or completely fluorinated $C_1$–$C_{20}$ aliphatic group, provided that at least one of $R^{1a}$ to $R^{1d}$ is a partially or completely fluorinated $C_1$–$C_{20}$ aliphatic group; and n is a number of 1 to 20.

2. A cosmetic comprising 0.01 to 100% by weight of a fluorine-containing oil (II) represented by the general formula:

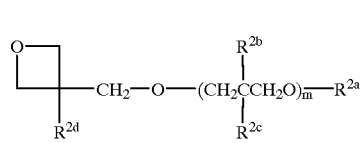

wherein $R^{2a}$ represents a hydrogen atom or a partially or completely fluorinated $C_1$–$C_{20}$ aliphatic group; $R^{2b}$, $R^{2c}$ and $R^{2d}$ represent a $C_1$–$C_{20}$ aliphatic group or a partially or completely fluorinated $C_1$–$C_{20}$ aliphatic group, provided that at least one of $R^{2a}$ to $R^{2d}$ is a partially or completely fluorinated $C_1$–$C_{20}$ aliphatic group; and m is a number of 1 to 20.

3. A cosmetic comprising 0.01 to 100% by weight of a fluorine-containing oil (III) represented by the general formula:

wherein X represents a hydrogen atom, a fluorine atom, a chlorine atom, a bromine atom or a partially or completely fluorinated $C_1$–$C_{30}$ aliphatic group; Y represents a partially or completely fluorinated $C_1$–$C_{30}$ aliphatic group; and $R^3$ represents a $C_1$–$C_{22}$ aliphatic group; and h+o=1 to 100.

4. A cosmetic comprising 1 to 30% by weight of at least one selected from the group consisting of fluorine-containing oils (I), (II) and (III) and 5 to 95% by weight of powder treated with a fluorine-containing compound.

* * * * *